United States Patent
Silvian

(10) Patent No.: US 6,577,900 B1
(45) Date of Patent: Jun. 10, 2003

(54) HIGH SPEED TELEMETRY SYSTEM

(75) Inventor: Sergiu Silvian, La Crescenta, CA (US)

(73) Assignee: Pacesetter, Inc., Sylmar, CA (US)

( * ) Notice: Subject to any disclaimer, the term of this patent is extended or adjusted under 35 U.S.C. 154(b) by 233 days.

(21) Appl. No.: 09/870,340

(22) Filed: May 29, 2001

(51) Int. Cl.⁷ .................................................. A61N 1/08
(52) U.S. Cl. .......................................... 607/60; 607/32
(58) Field of Search .................... 607/30–34, 59–61; 128/903

(56) References Cited

U.S. PATENT DOCUMENTS

| | | | |
|---|---|---|---|
| 4,408,607 A | 10/1983 | Maurer | 128/419 R |
| 4,944,299 A | 7/1990 | Silvian | 128/419 PG |
| 4,980,898 A | 12/1990 | Silvian | 375/59 |
| 5,591,217 A | 1/1997 | Barreras | 607/61 |
| 5,769,877 A | 6/1998 | Barreras, Sr. | 607/61 |
| 5,807,397 A | 9/1998 | Barreras | 607/61 |
| 5,999,857 A | * 12/1999 | Weijand et al. | 607/60 |

* cited by examiner

*Primary Examiner*—Jeffrey R. Jastrzab

(57) ABSTRACT

A telemetry system for use in an implantable device that communicates with an external programmer, includes a coil, a timing circuit connected to the coil, and a coil driver circuit that reverts at least part of the expanded energy back to the power source. The timing circuit generates two control signals SC1 and SC2, and is comprised of four switches S1, S2, S3, S4 that are connected across the power source and the coil, and that are selectively energized by the control signals SC1 and SC2. The control signal SC1 energizes switches S1 and S4 to close, with the switches S2 and S3 open, causing the coil to become a load across the power source and to store energy therefrom. Upon the expiration of the control signal SC1, the control signal SC2 triggers switches S2 and S3 to close with the switches S1 and S4 open, causing the coil to discharge the stored energy through the power source, charging it.

22 Claims, 8 Drawing Sheets

HIGH SPEED TELEMETRY SYSTEM

FIELD OF THE INVENTION

The present invention relates generally to cardiac pacemakers, and other types of implantable medical devices that can be programmed and/or analyzed following implantation using an external diagnostic/programmer system. Particularly, the invention relates to a high-speed digital telemetry system for use in implantable devices. More specifically, the present invention relates to an implantable telemetry transmitter and corresponding external receiver that utilize a coil driver circuitry with power savings feature for minimizing power consumption.

BACKGROUND OF THE INVENTION

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of causing a desired response. Implantable medical devices such as pacemakers, perform both observational and regulatory functions, i.e., they monitor the heart to ensure it beats at appropriate intervals; and if not, they cause an electrical stimulation pulse to be delivered to the heart in an attempt to force the heart to beat at an appropriate rate.

In order for an implantable device to perform its functions at minimum inconvenience and risk to the person or animal within whom it is used, some sort of noninvasive telemetry means must be provided that allows data and commands to be easily passed back and forth between the implantable device and an external device. Such an external device, known by a variety of names, such as a controller, programmer, or monitor, provides a convenient mechanism through which the operation of the implantable device can be controlled and monitored, and through which data sensed or detected by the implantable device can be transferred out of the implantable device to an external (non-implanted) location where it can be read, interpreted, or otherwise used in a constructive manner.

As the sophistication and complexity of implantable devices has increased in recent years, the amount of data that must be transferred between an implantable device and its accompanying external device or programmer, has dramatically increased. This, in turn, has resulted in a search for more efficient ways to effectuate such a data transfer at high speed. The telemetry must not only transfer the desired data without significant error, but it must do so at a high speed while preserving the limited power resources of the implanted device.

The problem of increasing the data transfer speed is directly affected by the power consumption of the implanted device. Typically, an implanted device has limited power capability and, due to its limited physical dimensions, allows for limited complexity of the electronic circuitry it can incorporate.

For example, a telemetry system with a data transfer speed of 8 kbps (kilobits-per-second), more exactly 8192 bps, is described in U.S. Pat. No. 4,944,299 to Silvian. It uses a carrier frequency of 8192 Hz, frequency selected to be higher than a computer monitor vertical sweep generator fundamental and its harmonics, and below the horizontal sweep generator fundamental. A computer monitor Electromagnetic Interference (EMI) is considered to be a main source of interference.

The 8 kbps telemetry system uses 1 bit per symbol and further uses a combined Amplitude Modulation (AM) and Phase Shift Keyed (PSK) modulation to limit the necessary bandwidth. The Phase Shift Keyed modulation tends to be resistant to noise because the data are encoded by means of changes in phase.

To use a carrier at 8 kbps and still increase the data transfer rate typically requires the use of more sophisticated electronics. While the design of such a system is feasible, it should be realized that this system will be implanted, in part, in an active live person. A live person has small surface movements due to respiration, heartbeats, etc. As the distance between the implant and the telemetry wand varies, so does the signal amplitude, which adds noise while demodulating finely defined amplitude levels.

An Automatic Gain Control (AGC) will minimize this effect but may not eliminate it completely. From a practical standpoint, the carrier frequency has to be increased. The following considerations have to be considered in selecting the higher carrier frequency. The implant titanium can act approximately as a 1-pole low pass filter with a −3 dB point at 10–20 KHz. The signal above this point is attenuated as 20 dB/decade frequency, and consequently the internal power will have to be increased in the same proportion.

However, the internal power of the implanted device has to be increased more than the 20 dB/decade frequency because the carrier frequency lies within a monitor horizontal display generator and/or its harmonic. Modern monitors utilize a fundamental frequency anywhere between 16 and 75 kHz. For a 64 kbps telemetry system, a compromise is made and a carrier can be selected around 100 KHz, which is above the fundamental of the horizontal generators.

The harmonics of the horizontal generators may or may not be present at this frequency. Both, the useful 100 KHz carrier and the horizontal generator harmonics at this frequency will be attenuated by the titanium can in the range of 14 dB to 20 dB. Taking into consideration the possibility of a computer monitor interference as explained above, the transmission level at a 100 kHz carrier should be significantly higher when compared to an 8 kbps system. However, in order to render such design practical, the power source of the implanted device must be preserved.

Therefore, there is a great and still unsatisfied need for a telemetry system that allows for a high data transfer of information while minimizing the power consumption of the implanted device.

SUMMARY OF THE INVENTION

The present invention addresses these and other concerns by providing an improved telemetry system. According to a preferred embodiment, the implantable telemetry system allows a high speed transfer of digital data by minimizing the power consumption of the implanted device.

The telemetry system accomplishes this goal without increasing the complexity of the circuitry, and without significantly increasing the overall cost of the implanted device.

The foregoing and other features of the present invention are achieved by a telemetry system that communicates with an implantable device, the implantable device including a coil driver circuit to revert at least part of the expanded energy back to the power source. The implantable telemetry system further includes a timing circuit that generates two control signals SC1 and SC2.

The coil driver is comprised of four switches S1, S2, S3, S4 that are connected across the power source and the coil, and that are selectively energized by the control signals SC1 and SC2. The control signal SC1 energizes switches S1 and S4 to close, with the switches S2 and S3 open, causing the coil to become a load across the power source and to store energy therefrom.

Upon the expiration of the control signal SC1, the control signal SC2 triggers switches S2 and S3 to close with the switches S1 and S4 open, causing the power source to become a load across the coil, and the coil to discharge the stored energy through the power source charging it. In this way a large part of the coil stored energy is returned to the power source and a bypass capacitor Cbypass connected across the power source.

According to one embodiment of the present invention, the control signal SC1 is a pulse with a width $T_1$, and the control signal SC2 is a pulse with a width $T_2$, such that the pulse widths (or duration) of the two control signals SC1 and SC2 are related by the following equation:

$$T_1 + T_2 \leq T,$$

where T is the duration of a single bit.

According to an alternative embodiment, the coil driver circuit includes a resonant circuit comprised of the coil and a capacitor C which is selectively connected across the coil. A switch S21 is connected between the power source and the capacitor C, and a switch S22 is connected across the coil and the power source. A diode is connected across the switch S22, for limiting the current flow to a single direction.

In this alternative embodiment, the control signal SC1 triggers the switch S21 to close with the switch S22 open, causing the capacitor to become a load across the power source and to be charged. The control signal SC2 triggers the switch S22 to close with the switch S21 open, causing the capacitor to sinusoidally discharge the capacitor C through the coil.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, in which:

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
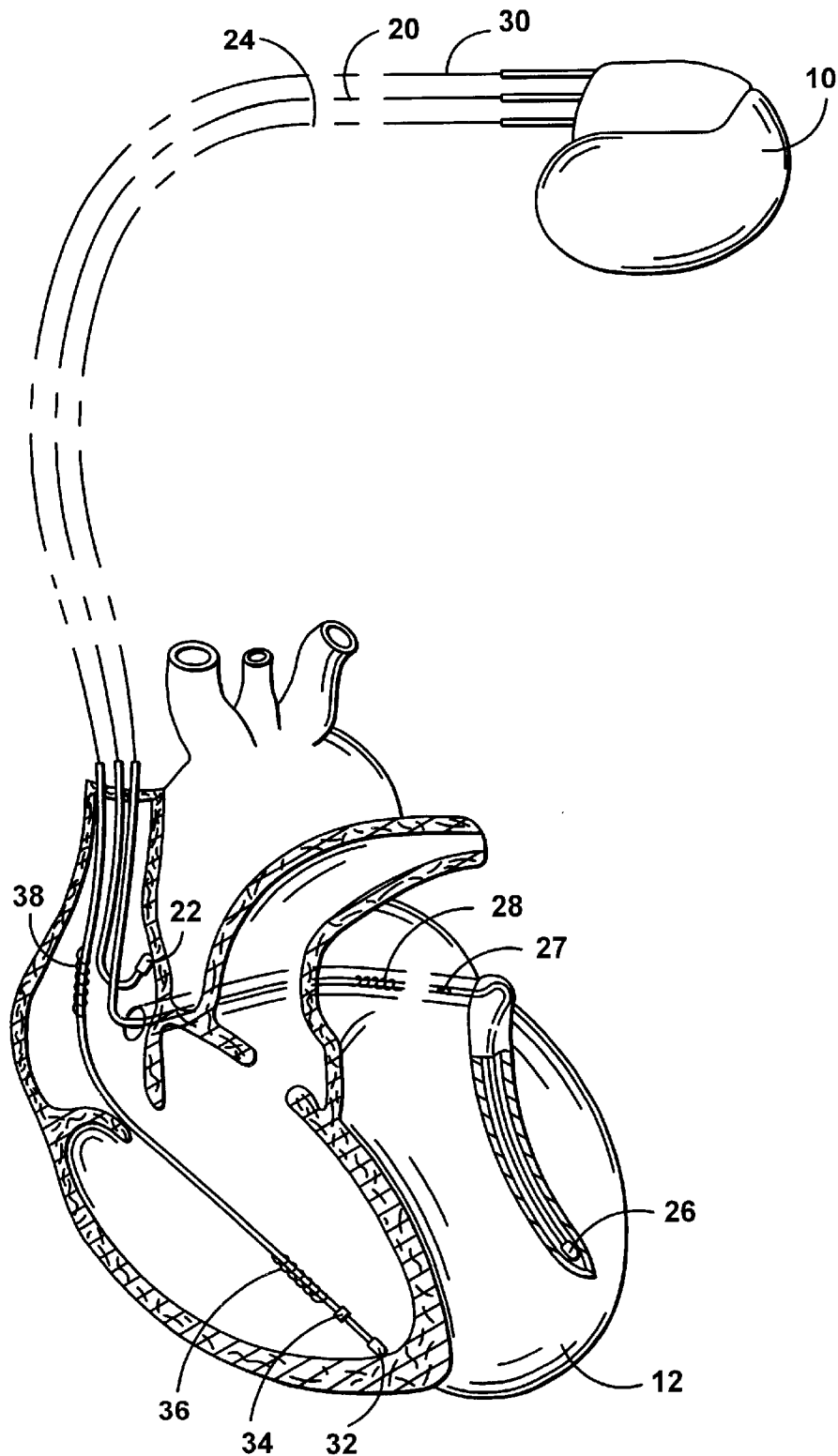
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
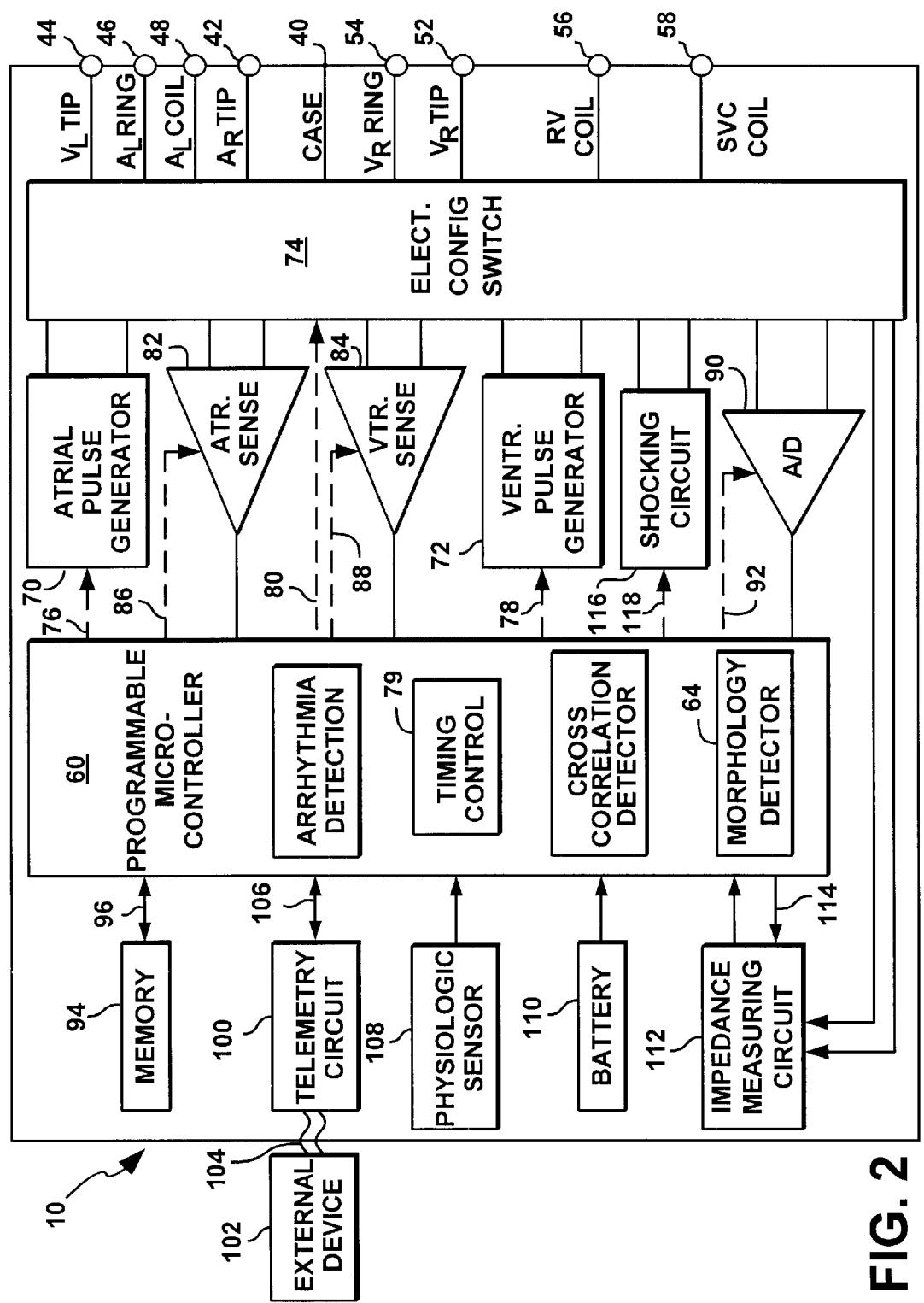
FIG. 2 is a functional block diagram of the multi-chamber implantable stimulation device of FIG. 1, illustrating the basic elements that provide cardioversion, defibrillation and/or pacing stimulation in four chambers of the heart, shown in telemetry communication with an external device/programmer.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the stimulation device 10 is the ability to sense and store a relatively large amount of data (e.g. from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
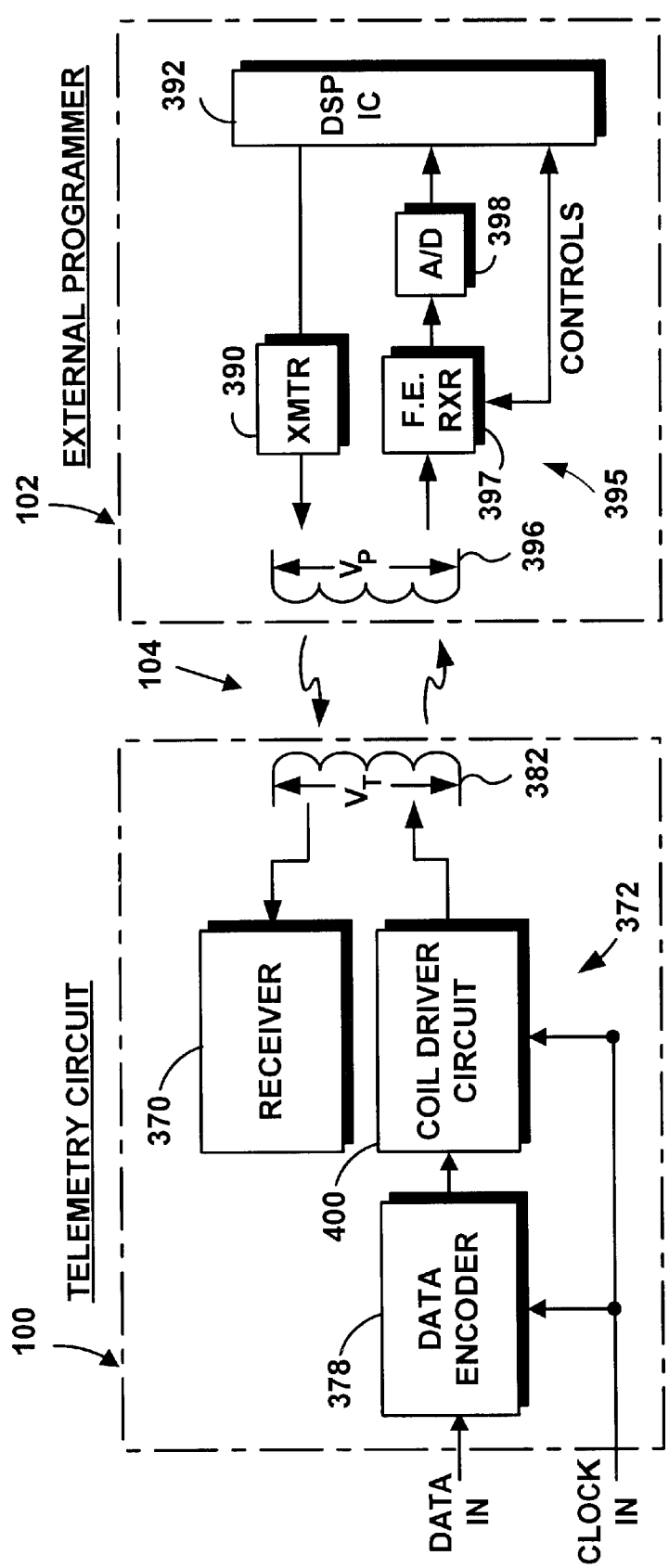
FIG. 3 is a high level schematic diagram of a telemetry system of the present invention, shown including a coil driver circuit.

FIG. 3 illustrates the implanted telemetry circuit 100 in communication with the external programmer 102 by way of the telemetry link 104. The telemetry circuit 100 includes a receiver 370 and a transmitter 372. The receiver 370 communicates data with the external programmer 102 over a coil 382. The transmitter 372 is generally comprised of a data encoder 378 and a coil driver circuit 400. Input data (DATA IN) are fed to the transmitter 372 where they are encoded by the encoder 378, and transmitted by the coil 382 to the external programmer 102, via a coil driver circuit 400. A clock signal (CLOCK IN) controls the clock signals to the telemetry circuit 100.

The external programmer 102 uses a bidirectional, dual-mode telemetry link, to communicate with the telemetry circuit 100. In a first mode, the external programmer 102 transmits data at a high (e.g. 65536 Hz) or normal bit rate (e.g. 8192 Hz) to the stimulation device 10, and in a second mode, it receives data at 64 kbps from the implanted telemetry circuit 100.

To this end, the external programmer 102 includes a transmitter 390 that uses an intelligent controller (or DSP chip) 392, to transmit data according to the command selected by the physician, by way of a telemetry wand coil 396.

The external programmer 102 further includes a receiver 395 which is comprised of a front end receiver 397 that receives data from the transmitter 372 of the implanted telemetry circuit 100, by way of the coil 396. The processed signals are then passed through an analog to digital converter 398 to digitize the signals before they are processed by the controller 392.

When the physician wishes to interface with the stimulation device 10, the physician positions the external programmer 102 as close as possible to the stimulation device 100 (e.g., within a few inches) so that the coil 396 of the external programmer/device 102 is located in proximity to the coil 382 of the telemetry circuit 100.

Figure 6A:
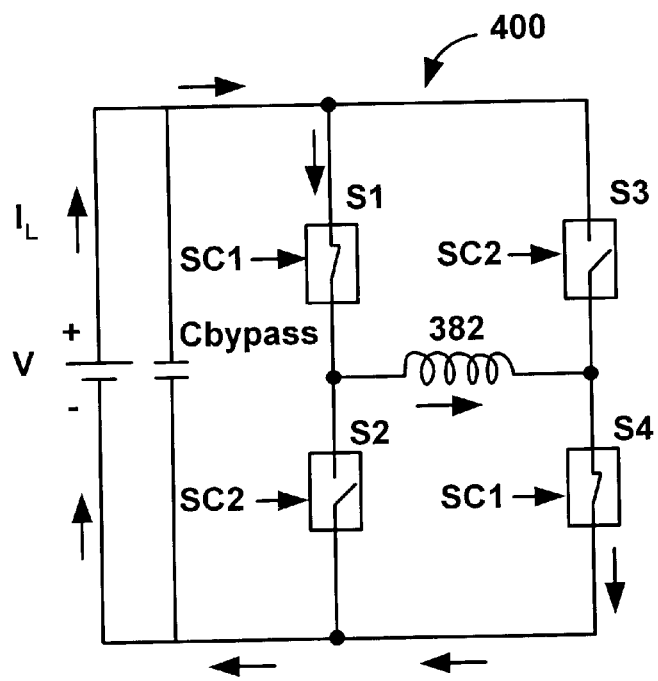
FIG. 6 is comprised of FIG. 6A and FIG. 6B, and represents a circuit diagram of the coil driver circuit of FIG. 3.
Figure 6B:
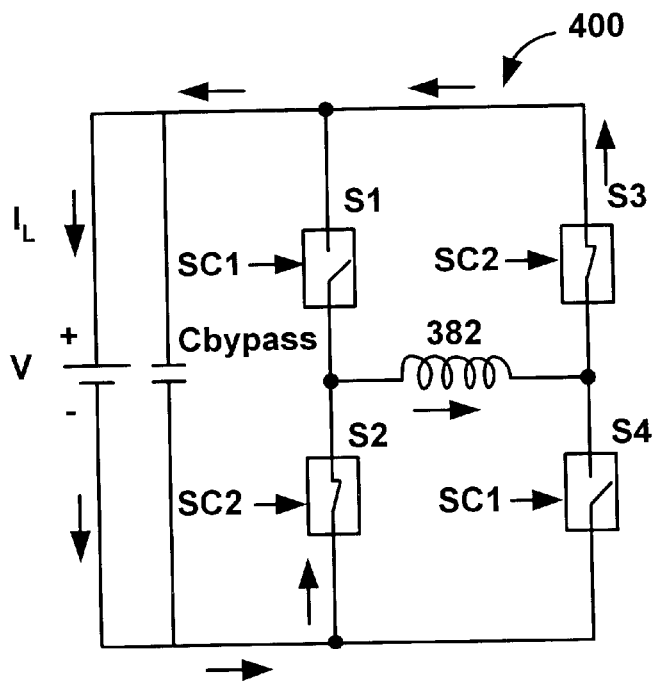

In order to preserve energy, the implanted telemetry circuit 100 is provided with a coil driver circuit 400. With further reference to FIGS. 6A and 6B, the coil driver circuit 400 is comprised of four switches S1, S2, S3, S4 that are connected across the power source (e.g. a battery) V and a capacitor Cbypass and controlled by control signals SC1 and SC2, as it will be described later in greater detail.

The external programmer 102 sends the desired command to the implanted stimulation device 10, and receives a response therefrom, using the two inductively coupled coils 382 and 396, with a voltage signal $V_T$ appearing across the coil 382, and a voltage signal $V_P$ appearing across the coil 396 of the external programmer 102 (FIG. 3). The two coils 382 and 396 thus function much the same as an air coil transformer, with the voltage applied to the one coil is transferred to the other coil as a function of the coupling coefficient between the two coils 382, 396, which coupling coefficient is highly dependent upon the separation distance between the two coils and the medium separating the two coils 382, 396. In one embodiment, the coil 396 has an inductance of approximately 300 $\mu$H.

Figure 4:
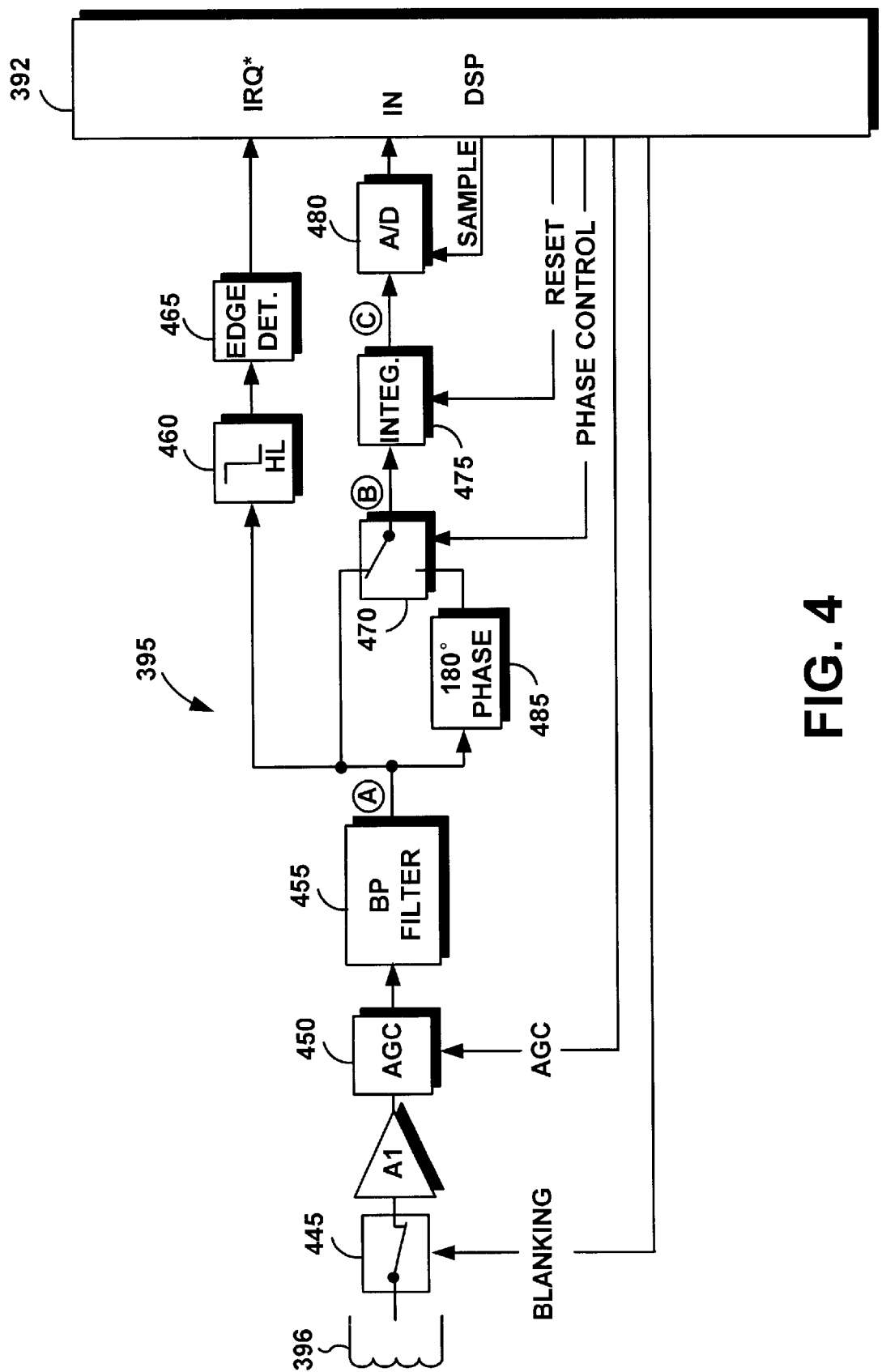
FIG. 4 is a more detailed circuit diagram of a receiver that forms part of the external programmer of FIG. 3.
Figure 8:
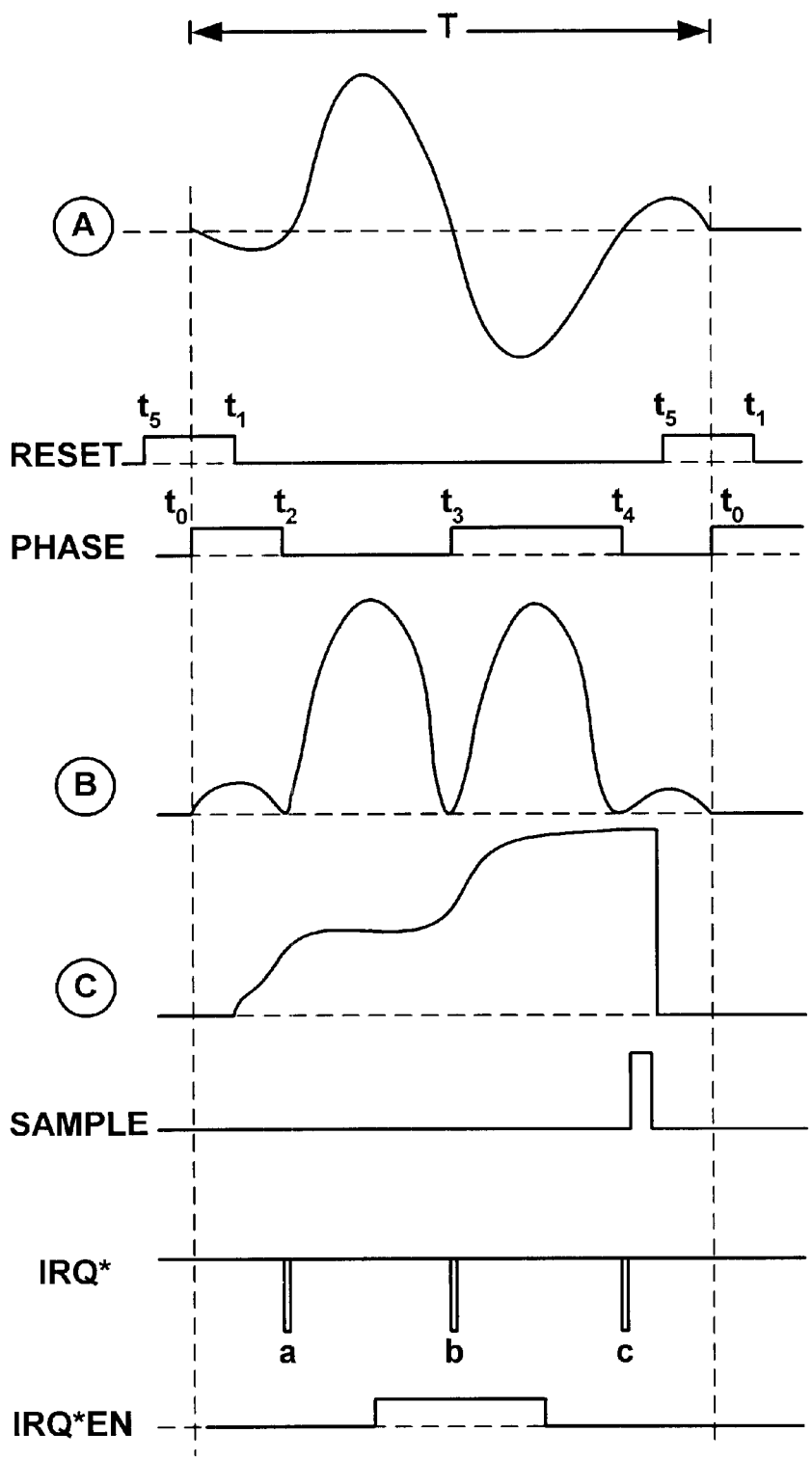
FIG. 8 represents timing diagrams signals of the receiver circuit of FIG. 4.

With reference to FIGS. 3, 4, and 8, input data (DATA IN) in the telemetry circuit 100 are synchronously encoded, and an information packet is modulated and transmitted to the external programmer 102. The signal transmitted to the external programmer 102 is received by the inductive coil 396 and processed by the front end receiver 397.

The elements of the front end receiver are illustrated in FIG. 4. A switch 445, which is normally closed, is operated by the Digital Signal Processor (DSP) or controller 392. When receiving data, switch 445 connected between the coil 396 and the amplifier A1 allows signal flow into the receiver 395. The received signal is amplified by the amplifier A1. While the programmer is in transmit mode and activates transmitter 390, the controller asserts signal BLANK which opens switch 445 to isolate the coil 396 from the amplifier A1, and to protect it from saturation.

A bandpass filter 455 with a bandwidth ranging between approximately 100 KHz and 150 KHz filters the signal. The bandpass filter rejects frequencies below 100 KHz and frequencies above 150 KHz. The filtered signal is sent to a hard limiter (HL), which is in essence a comparator circuit, that outputs a binary 1 when its input is positive and a 0 when its input is negative. The signal at the output of the hard limiter 460 is sent to an edge detector 465 that generates short duration active-low pulses when signal A zero crosses. The zero crossings are fed to the Interrupt Request bar (IRQ*) input of the controller 392, to be used as explained herein.

The controller 392 controls a two-way switch 470. In a first position, the switch 470 allows the output of the bandpass filter 455 to be passed directly through to an integrator 475, and therefrom to an analog-to-digital converter 480. In turn, the analog-to-digital converter 480 presents the result of the conversion in a serial bit stream to an IN input of the controller 392.

In a second position, the switch 470 passes the output of the bandpass filter 455 through a 180-degree phase shift circuit 485, and therefrom to the analog-to-digital converter 480 and to the IN input of the controller 392. As a result, the switch 470 and the phase shift circuit 485 effectively simulate the role of a full wave rectifier.

FIG. 8 represents various timing diagrams illustrating the responses of the receiver 395 of FIG. 4. The graph labeled "A" represents the signal at the output of the bandpass filter 455. The controller 392 issues a RESET signal during the interval from time t5 of the prior bit to time t1 of the present bit, to reset the integrator 475. It should be apparent that the controller 392 is programmed to switch phase at timing t0, t2, t3 and t4 when signal "A" is expected to have zero crossings. The PHASE signal is used to invert the negative portions of the sinusoidal wave, rendering it unipolar. The Interrupt Request (IRQ*) of the controller 392 receives the train of interrupt pulses: "a", "b", and "c".

The controller 392 is programmed to enable the interrupt only during the time duration around pulse "b" and to reject the interrupt during the time duration around pulses "a" and "c" according to an internal signal IRQ*EN. When the interrupt pulse "b" occurs, the controller 392 stores the interrupt time from the start of the bit. Later, it compares it with half the bit duration (T/2). If the interrupt occurs earlier, the controller 392 adjusts an internal PLL (phase-locked-loop) to slow the 64 k clock signal. Otherwise, if the interrupt occurs later, the controller 392 adjusts the 64 k clock to speed up the 64 k clock to a faster rate.

In graph "B", the input signal to the integrator 475 is fully rectified. The integrator 475 then integrates the half sinusoidal signal.

The integrated signal is shown in graph "C". It should be noted that graph "B" is a block diagram presentation, as the real circuit of an integrator using an op-amp inverts the signal. The "RESET" pulses resets the integrator 475 and prepares it for the next bit. The analog-to-digital (A/D) converter 480 samples the integrated signal (graph "C") peak and digitizes it for the controller 392 to compare it to a reference value equal to half the signal "C" peak. If the digitized signal is lower than the reference value, then it is stored as a "0", otherwise, it is stored as a "1".

The controller 392 also compares the signal "C" sampled peak with a reference stored value and performs an automatic gain control (AGC) by adjusting the level of the signal AGC to maintain a constant signal amplitude. The controller 392 includes a digital-to-analog converter (not shown) since the signal AGC is an analog signal. Alternatively, a separate digital-to-analog converter can be added.

Having described the main components and the method of use of the implanted telemetry circuit 100 and the programmer 102 receiver, the implanted telemetry circuit 100 will now be described in more detail in connection with FIG. 5 through FIG. 7.

Figure 5:
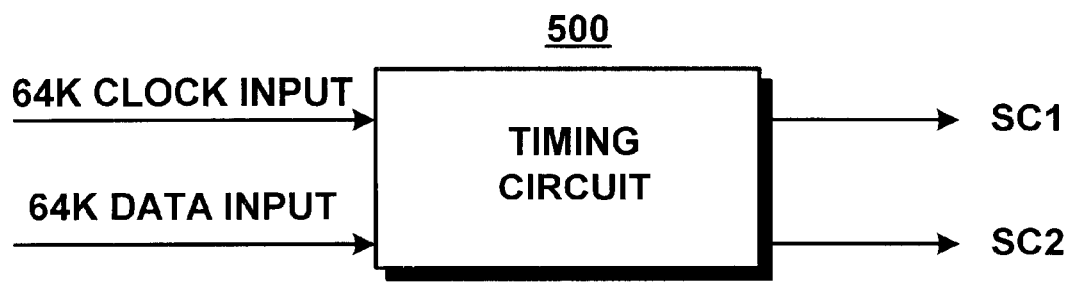
FIG. 5 represents a block diagram of a timing circuit used in the telemetry system of FIG. 3, shown provided with two inputs: a 65536 kHz Clock input and a 64 Kbps (exactly 65536) Data input, for generating two control signals SC1 and SC2.

FIG. 5 represents a block diagram of a timing circuit 500 forming part of the implanted stimulation device 10. The timing circuit 500 has two inputs: a 64 kHz Clock input, and a 64 kbps Data input. The timing circuit 500 generates two output control signals SC1 and SC2 to control the coil driver 400.

Figure 7:
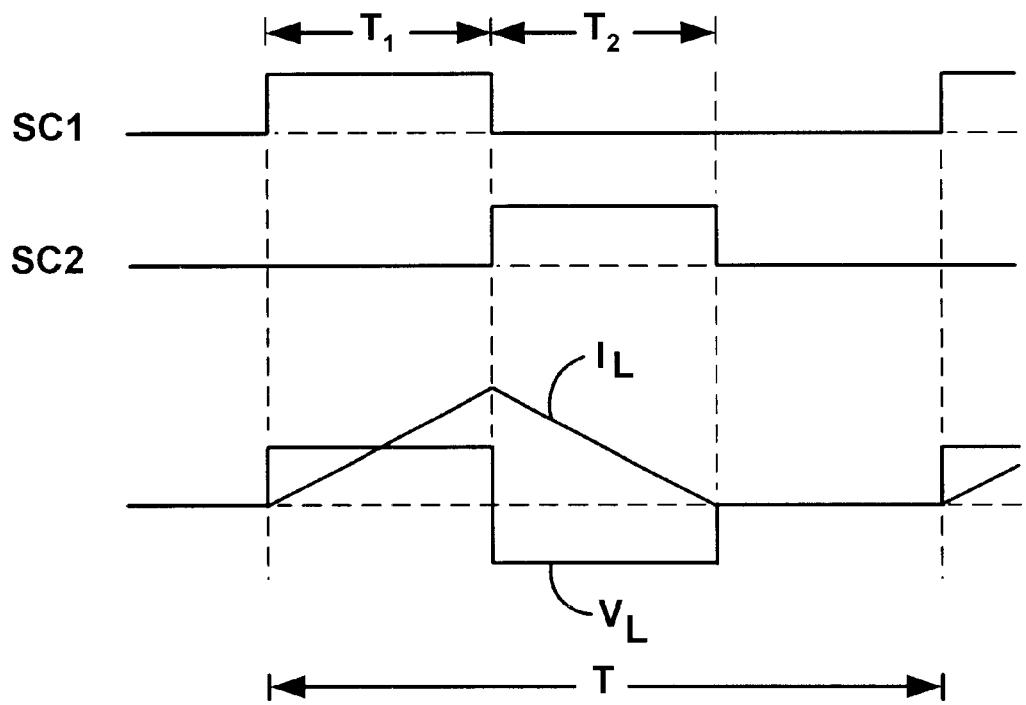
FIG. 7 illustrates timing charts for the coil driver circuit of FIG. 6.

Considering that the pulse width of control signal SC1 is $T_1$, and the pulse width of the control signal SC2 is $T_2$, the pulse widths of the two control signals SC1 and SC2 are related by the following equation:

$$T_1 + T_2 \leq T.$$

where T is the bit duration in (FIGS. 7 and 8). The sum of the two pulse widths $T_1$ and $T_2$ is selected to be less than the period T in order to allow sufficient time for transients of the prior bit to decay, before processing a new bit.

FIGS. 6A and 6B illustrate the operation of the coil driver circuit 400. Without the coil driver circuit 400, valuable energy would be wasted when the coil 382 is disconnected since, if a simple coil driver with only a single switch connected between the power source and the coil with the common terminals of the power source and the coil coupled, were used, this switch closes during the period $T_1$, allowing the coil 382 to store energy. During the next period $T_2$, the switch opens and the stored energy is dissipated in transients around the coil 382. The present invention resolves this waste of energy problem, and returns most of the energy stored in the coil 382 back to the power source and the capacitor Cbypass, as explained further.

With reference to FIG. 6A, the control signal SC1 controls switches S1 and S4 to close while the switches S2 and S3 remain open. Whereupon, the coil 382 becomes the load across the power source V. The coil 382 stores energy from the power source V in the form of a magnetic field. With reference to FIG. 7, the pulse width of the control signal SC1 is $T_1$.

Upon expiration of the control signal SC1, the switches S1 and S4 are open, and the second control signal SC2 is applied to the coil driver circuit 400. With reference to FIG. 7, the pulse width of control signal SC2 is $T_2$.

As illustrated in FIG. 6B, the control signal SC2 controls the switches S2 and S3 to close while the switches S1 and S4 remain open. Whereupon, the polarity of the coil 382 with respect to the power source becomes inverted, causing the energy stored in the coil 382 to be channeled back to power source, charging it. It should be noted that in sending binary information, i.e., bits of "0" and "1", the coil 396 is energized only when a "1" is transmitted.

FIG. 7 illustrates the timing charts for the coil driver circuit 400 of FIG. 6 for ideal switches and coil without losses, the pulse width $T_2$ should be slightly smaller than the pulse width $T_1$. In one example, the pulse widths $T_1$=5.2 $\mu$s, $T_2$=4.7 $\mu$s and T=15.3 s.

In one bit duration T, and as described earlier, the control signal SC1 energizes switches S1 and S4, closing them and connecting the coil 382 (FIG. 6A) across the voltage source V. The current, $I_L$, passing through the coil 382 increases linearly during the SC1 pulse width $T_1$. The coil 382 induces a magnetic field to store energy from the power source V.

The termination of the control pulse SC1 de-energizes the switches S1 and S4. The control signal SC2 triggers the switches S2 and S3 to close, inverting the coil connection across the power source V. This, in turn, reverses the role of power source V and the coil 382, wherein the coil 382 arts as a power source while the battery acts as a load.

The energy stored in the coil 382 is directed back to the battery (and the capacitor Cbypass) where it is stored by recharging the battery (and the capacitor Cbypass). The current, $I_L$, flowing through the coil 382 decreases linearly to zero during the pulse width $T_2$.

During $T_1$ and $T_2$, the voltage, $V_L$, across the coil 382 is proportional to the change in the coil current, $I_L$, with respect to time, as shown in the following equation:

$$V_L = dI_L/dt.$$

As a result, the coil voltage $V_L$ is the derivative of the wave form of the coil current $I_L$.

Figure 9:
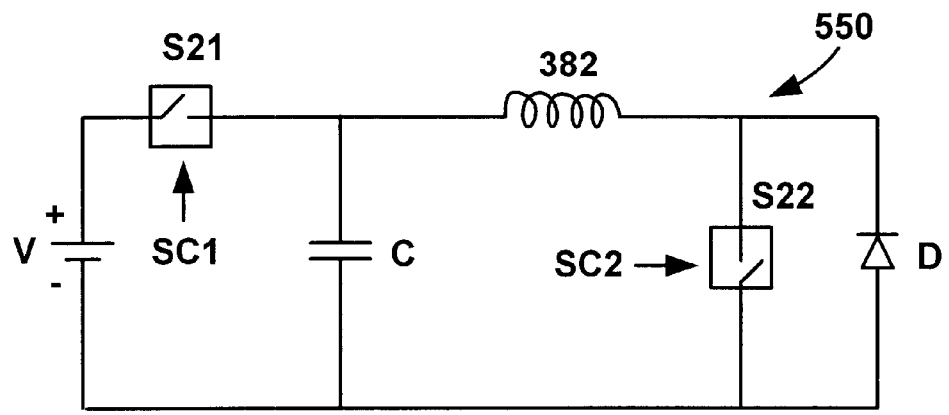
FIG. 9 is a circuit diagram of another embodiment of the coil driver circuit of FIG. 3.

FIG. 9 is a circuit diagram of another coil driver circuit 500 according to the present invention. The coil driver circuit 500 utilizes a resonant circuit (LC), and further comprises two switches S21 and S22. Compared to the coil driver circuit 400, the coil driver circuit 500 includes half the number of switches.

The control signal SC1 controls the switch S21 to close, and the control signal SC2 controls the switch S22 to close. When the switch S21 is closed, the capacitor C is connected across the power source V, and accumulates charge until the voltage, $V_C$, across the capacitor C equals that of the power source V. When switch S22 closes (with the switch S21 open), it shorts the diode D, allowing the capacitor C to dump its charge into the coil 382.

The coil current, $I_L$, starts to increase as the capacitor voltage, $V_C$, decreases. When the switch S22 opens, a negative coil current, $I_L$, is maintained by the diode D. As the coil current, $I_L$, reaches zero, the diode D stops conducting current and the cycle terminates. Capacitor C stores the last Vc voltage until it is replenished through the switch S22 during the period $T_1$.

Figure 10:
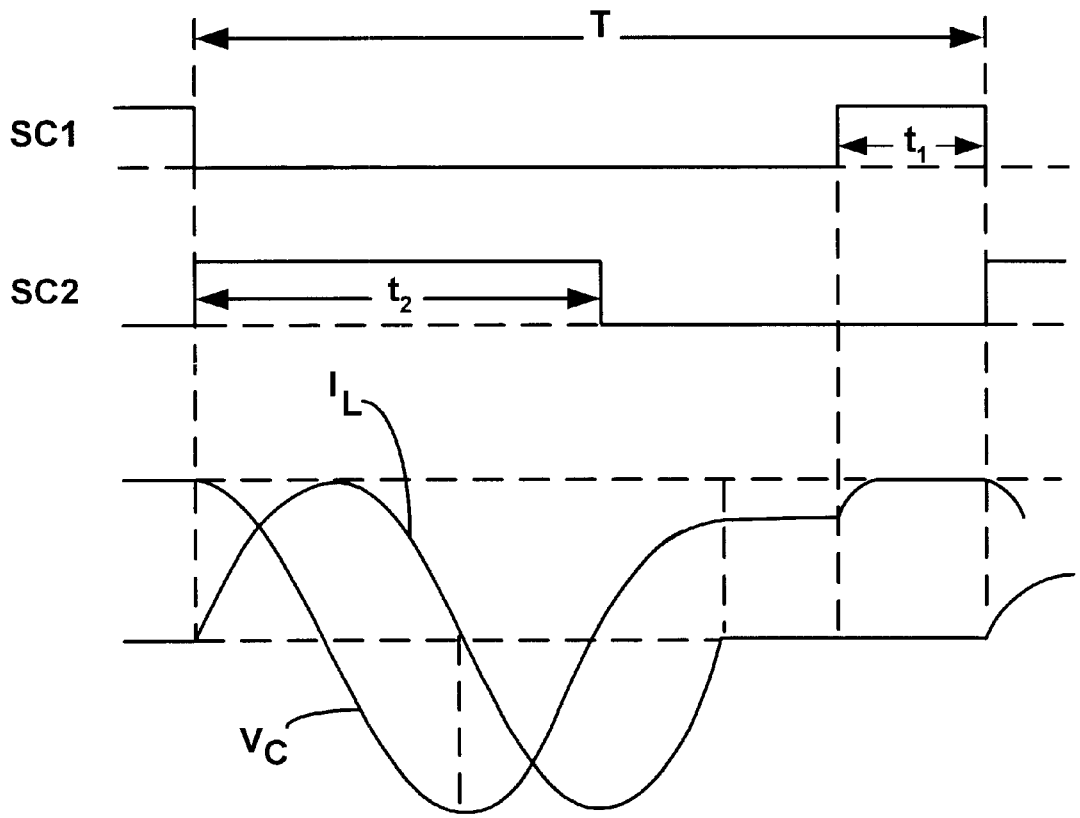
FIG. 10 represents timing diagrams illustrating the signals in the circuit of FIG. 9.

FIG. 10 represents various timing diagrams illustrating the signals of the coil driver circuit 440 of FIG. 9. The two control signals SC1 and SC2 are pulsed at mutually exclusive time intervals, $T_1$ and $T_2$, respectively. One period T is illustrated FIG. 10. The voltage, $V_L$, across the coil 382 is sinusoidal.

While certain preferred embodiments of the invention have been described, these embodiments have been presented by way of example only, and are not intended to limit the scope of the present invention.

The present telemetry system described so far uses amplitude shift keying (ASK) modulation. It should understood that other modulation schemes can be used such as phase shift keying (PSK) modulation in which the phase of the signal is modulated.

What is claimed is:

1. A telemetry system for use in an implantable stimulation device, the telemetry system comprising:
   a telemetry coil;
   an energy source that supplies energy to the telemetry coil;
   a telemetry coil driver circuit coupled between the telemetry coil and the energy source, wherein the coil driver circuit is configurable in at least two modes; and
   a timing circuit connected to the coil driver circuit, wherein the timing circuit is operative to control the coil driver circuit to assume the respective modes, wherein in one of the modes at least a part of the energy in the telemetry coil is returned back to the energy source.

2. The telemetry system according to claim 1, wherein the timing circuit generates first and second control signals to control the coil driver circuit to assume the respective modes.

3. The telemetry system according to claim 2, wherein the telemetry coil driver circuit comprises four switches configured as an H-bridge across the telemetry coil, and wherein the four switches are selectively energized by the first and second control signals.

4. The telemetry system according to claim 3, wherein the first control signal is a pulse with a width $T_1$;
   wherein the second control signal is a pulse with a width $T_2$; and
   wherein the pulse widths of the control signals are related by the following equation:

$$T_1 + T_2 \leq T,$$

where T is the duration of a single bit.

5. The telemetry system according to claim 4, wherein the first control signal cyclically closes a pair of said switches to cause the telemetry coil to become a load across the energy source.

6. The telemetry system according to claim 4, wherein the telemetry coil stores energy from the energy source; and
   wherein the second control signal closes a second pair of said switches to cause the telemetry coil to discharge stored energy into the energy source.

7. The telemetry system according to claim 4, wherein a "1" bit is transmitted by asserting the first control signal for a duration $T_1$ followed by the second control signal for a duration $T_2$; and
   wherein a "0" bit is transmitted by not asserting either of said control signals, causing said four switches to remain open during the entire "0" bit duration.

8. The telemetry system according to claim 4, wherein a "1" bit is transmitted asserting the first control signal for a duration $T_1$, followed by the second control signal for a duration $T_2$; and
   wherein a "0" bit is transmitted by asserting the second control signal for a duration $T_1$ followed by the first control signal for a duration $T_2$.

9. The telemetry system according to claim 2, wherein the telemetry coil driver circuit includes:
   a resonant circuit comprised of the telemetry coil and a capacitor which is selectively connected across the telemetry coil;
   a first switch connected between the energy source and the capacitor; and
   a second switch connected across the telemetry coil and the energy source.

10. The telemetry system according to claim 9, further including a device connected across the second switch that is operative to allow a current through the telemetry coil to flow in one direction.

11. The telemetry system according to claim 9, wherein the first control signal closes the first switch to cause the capacitor to become a load across the energy source and to be charged.

12. The telemetry system according to claim 11, wherein the second control signal cyclically closes the second switch to cause the capacitor to become an energy source and the telemetry coil to become a load across the capacitor, and the voltage and current in the telemetry coil and capacitor circuit to sinusoidally oscillate, discharging and then charging back the capacitor.

13. The telemetry system according to claim 1 for use with an external programmer, and wherein the programmer includes:
   a bandpass filter; and
   a synchronous demodulator that demodulates signals received from the implantable device.

14. The telemetry system according to claim 13, wherein the programmer further includes an integrator that integrates the signal demodulated by the synchronous demodulator.

15. The telemetry system according to claim 14, wherein the programmer further includes a digitizer that samples and digitizes signals integrated by the integrator.

16. The telemetry system according to claim 12, wherein the synchronous demodulator includes a switch and a phase shift circuit.

17. The telemetry system according to claim 12, wherein the programmer further includes a zero-crossing detector on the received signal that generates a controller interrupt.

18. The telemetry system according to claim 17, wherein the zero-crossing detector includes a hard limiter.

19. A telemetry system for use in an implantable stimulation device, the telemetry system comprising:
   a telemetry coil;
   an energy source that supplies energy to the telemetry coil;
   a switching circuit coupled between the energy source and the telemetry coil, and adapted to selectively couple the energy source to the telemetry coil in at least two configurations; and
   a timing circuit coupled to the switching circuit for controlling the coupling of the energy source to the telemetry coil in the at least two configurations, so that at least a portion of the energy supplied to the telemetry coil is returned to the energy source when the switching circuit assumes one of the configurations.

20. A telemetry system for use in an implantable stimulation device comprising:
   telemetry coil means;
   energy means for supplying energy to the telemetry coil means; and
   switch means for switchably coupling the energy means to the telemetry coil means in at least two configurations for respectively providing energy to the telemetry coil and delivering at least a portion of the energy in the telemetry coil means to the energy means.

21. The telemetry system according to claim 20, further including timing means for generating first and second control signals;

wherein the switch means is comprised of four switches that are generally configured as an H-bridge across the telemetry coil means, and wherein the four switches are selectively energized by the respective first and second control signals to assume the respective configurations.

22. The telemetry system according to claim 21, wherein the first control signal cyclically closes a first pair of said switches, while a second pair of said switches remain open, causing the telemetry coil means to become a load across the energy means; and wherein the second control signal closes said second pair of switches, while the first pair of said switches remain open, causing the telemetry coil to discharge stored energy into the energy source.

* * * * *